United States Patent [19]

Schrader

[11] Patent Number: 5,460,973
[45] Date of Patent: Oct. 24, 1995

[54] METHOD FOR CONTINUOUS DETERMINATION OF VOLATILE IMPURITIES IN CONTAMINATED MEDIUM

[75] Inventor: Bernhard Schrader, Essen, Germany

[73] Assignee: CeramOptec Industries Inc., East Longmeadow, Mass.

[21] Appl. No.: 359,532

[22] Filed: Dec. 20, 1994

[51] Int. Cl.$^6$ ...................................................... G01N 21/00
[52] U.S. Cl. .......................... 436/167; 436/181; 436/177; 422/82.11; 359/123; 359/141
[58] Field of Search ..................................... 436/164, 167, 436/175, 177, 181, 38; 422/82.11; 359/123, 141

[56] References Cited

U.S. PATENT DOCUMENTS 5,059,396  10/1991  Opitz et al. ........................... 422/82.11

OTHER PUBLICATIONS

H. Heinrich et al; Determination of Organic Compounds by IR/ATR Spectroscopy with Polymer Coated Internal Reflection Elements; Appl. Spec. 44 1641–46 (1990).

*Primary Examiner*—Lyle A. Alexander
*Attorney, Agent, or Firm*—Bolesh J. Skutnik; Deborah Basile

[57] ABSTRACT

A method of optically measuring volatile impurities in contaminated medium using a combination of a distillation process with head space analysis. The method uses a hydrophobic extracting membrane at the surface of an internal reflection element (an optical fiber or an attenuated total reflection crystal). The hydrophobic analytes are extracted into the extracting membrane, from the contaminated medium. By heating the contaminated medium to form a vapor and cooling the sensor element surrounded by the extracting membrane this invention significantly reduces the limit of detection by between two and three orders of magnitude from the prior art. The distillation aspect of the method also serves to protect the extracting membrane surrounding the sensor from damage by the mechanical impurities in the contaminated medium. A simultaneous continuous analysis of several impurities of the contaminated medium is possible by several optical fibers arranged in parallel on the same cooling device, each of which is designed for another contaminate by means of optical filters, wavelengths disperging elements (gratings or prisms) or wavelength selective IR sources or detectors.

8 Claims, 4 Drawing Sheets

METHOD FOR CONTINUOUS DETERMINATION OF VOLATILE IMPURITIES IN CONTAMINATED MEDIUM

BACKGROUND OF THE INVENTION

1. Field of Invention

The present invention relates to an arrangement for optical measuring of volatile impurities in contaminated medium such as water.

2. Information Disclosure Statement

The determination of impurities in water (the analytes) by infrared spectroscopy is handicapped by the strong continuous absorption of water in the whole infrared range. U.S. Pat. No. 5,059,396 issued to Opitz et. al. in 1991 teaches an arrangement for optically measuring the concentration of substances in which a measuring space is provided of a material which is selectively permeable for substances to be measured and transparent for a measuring radiation and which is in operative connection with an object to be measured and through which the measuring radiation is transmitted. Opitz teaches the application of a hydrophobic extracting membrane as a measuring space at the surface of an internal reflection element, e.g. an optical fiber or an attenuated total reflection (ATR) crystal. Such an arrangement has the advantage that hydrophobic analytes are extracted into and enriched in the extracting membrane by factors between 10 and 100,000 while water is excluded. The infrared absorption of the substance in the extracting membrane is then measured by the so-called evanescent wave which emerges into the membrane under the condition of total reflection. Thus, continuous determinations are possible. The limit of detection, however, is still too high for many applications. Also, the extracting membrane may be destroyed by material contaminations, especially if the analyte to be measured is contained in waste water. The present application removes these difficulties.

The objectives of the invention are as follows: 1. To significantly reduce the detection limit of volatile impurities in a contaminated medium over the prior art. 2. To increase efficiency and decrease cost as the distillation process of the present invention protects against mechanical wear of the extracting membrane by excluding the abrasive components of the contaminated medium from the membrane. 3. To increase efficiency and decrease cost as the distillation process of the present invention reduces the chemical wear of the membrane by reducing its temperature. 4. To teach the use of alternatives to standard spectroscopy for measurement of analytes in a contaminated medium.

BRIEF SUMMARY OF THE INVENTION

The present invention provides a device and method for the measurement of volatile impurities in contaminated medium utilizing a combination of a distillation process with head space analysis, both acting continuously. By heating the contaminated medium to be analyzed to form a vapor and cooling the sensor element surrounded by an extracting membrane, the present invention reduces the limit of detection by between two and three orders of magnitude over the prior art. Since the operative connection between the sensor element and the contaminated medium to be analyzed is achieved via distillation, it also provides protection against damage to the extracting membrane surrounding the sensor by the mechanical impurities of the contaminated medium to be investigated which cannot be filtered out. Further, the present invention arrangement provides continuous washing of the membrane surrounding the sensor element membrane by the heated medium condensing together with the volatile analyte at the cooled sensor device. The present invention utilizes multiple measuring channels using optical fibers as internal reflection elements to allow for measurement and recording of several (e.g. five) different analytes simultaneously.

BRIEF DESCRIPTION OF THE DRAWINGS

The present invention should be more fully understood when the specification herein is taken in conjunction with the drawings appended thereto, wherein.

DETAILED DESCRIPTION OF PREFERRED EMBODIMENTS

Figure 1:
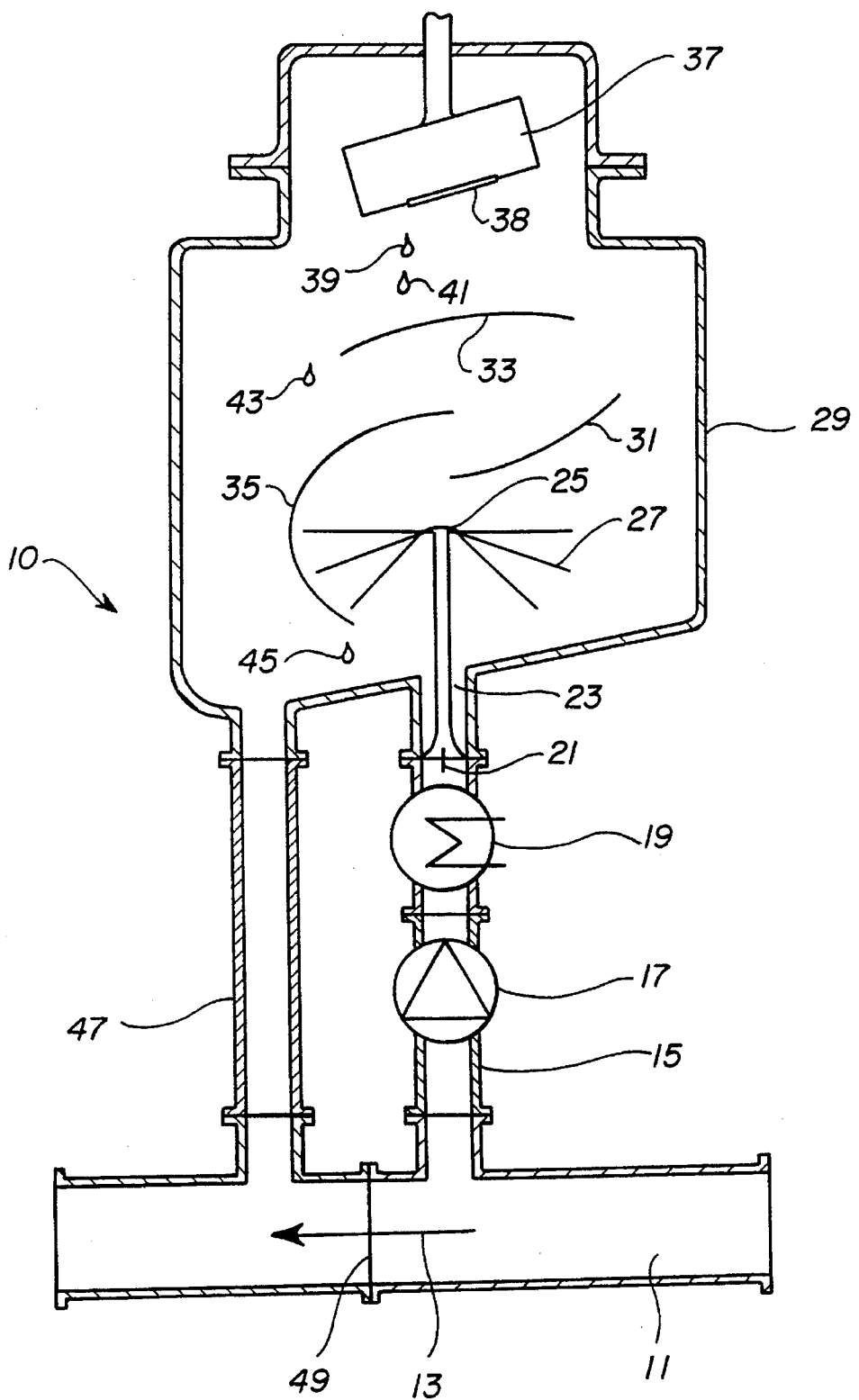
FIG. 1 shows a side cut view of a preferred embodiment of the present invention device combining distillation and head space analysis; and, FIG. 2 is a side cut view showing in detail the components of preferred embodiment of a sensor element of the present invention.
Figure 2:
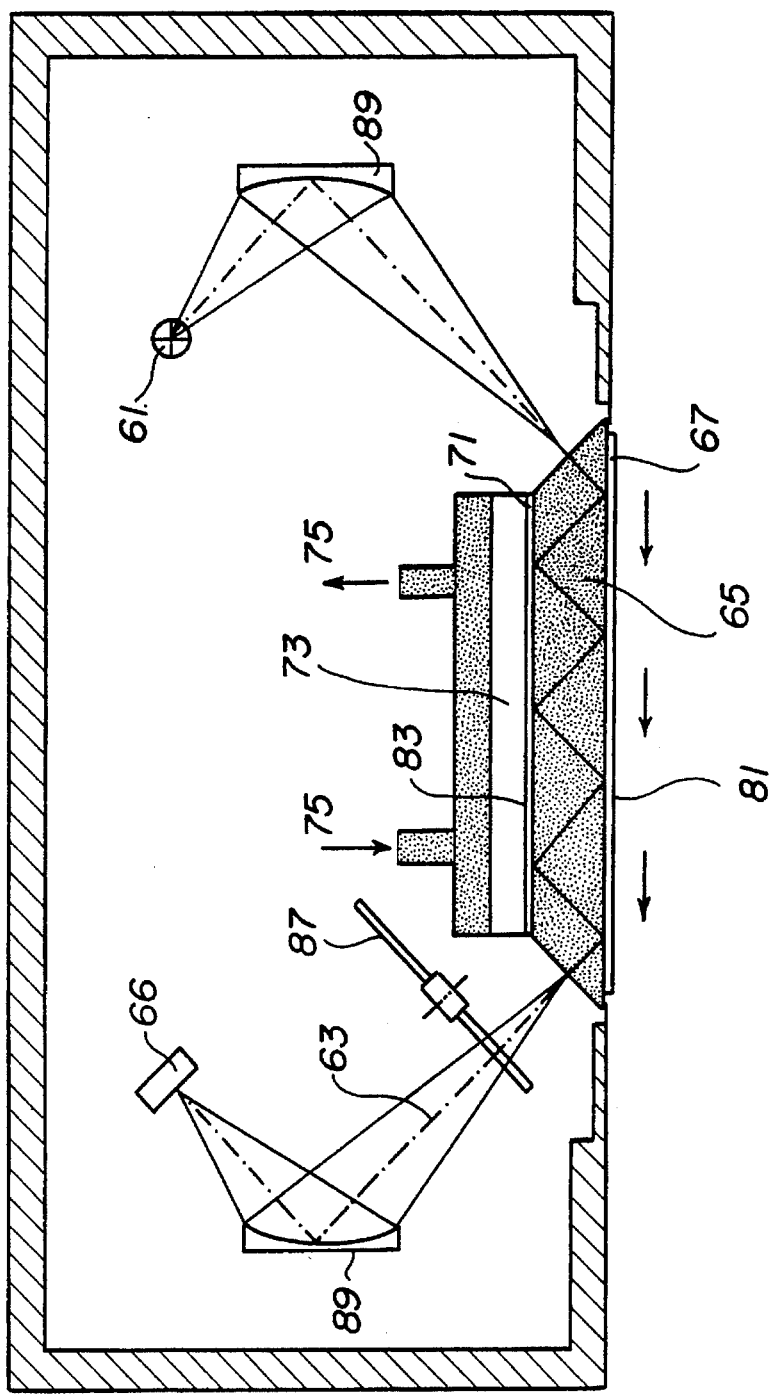
Figure 3:
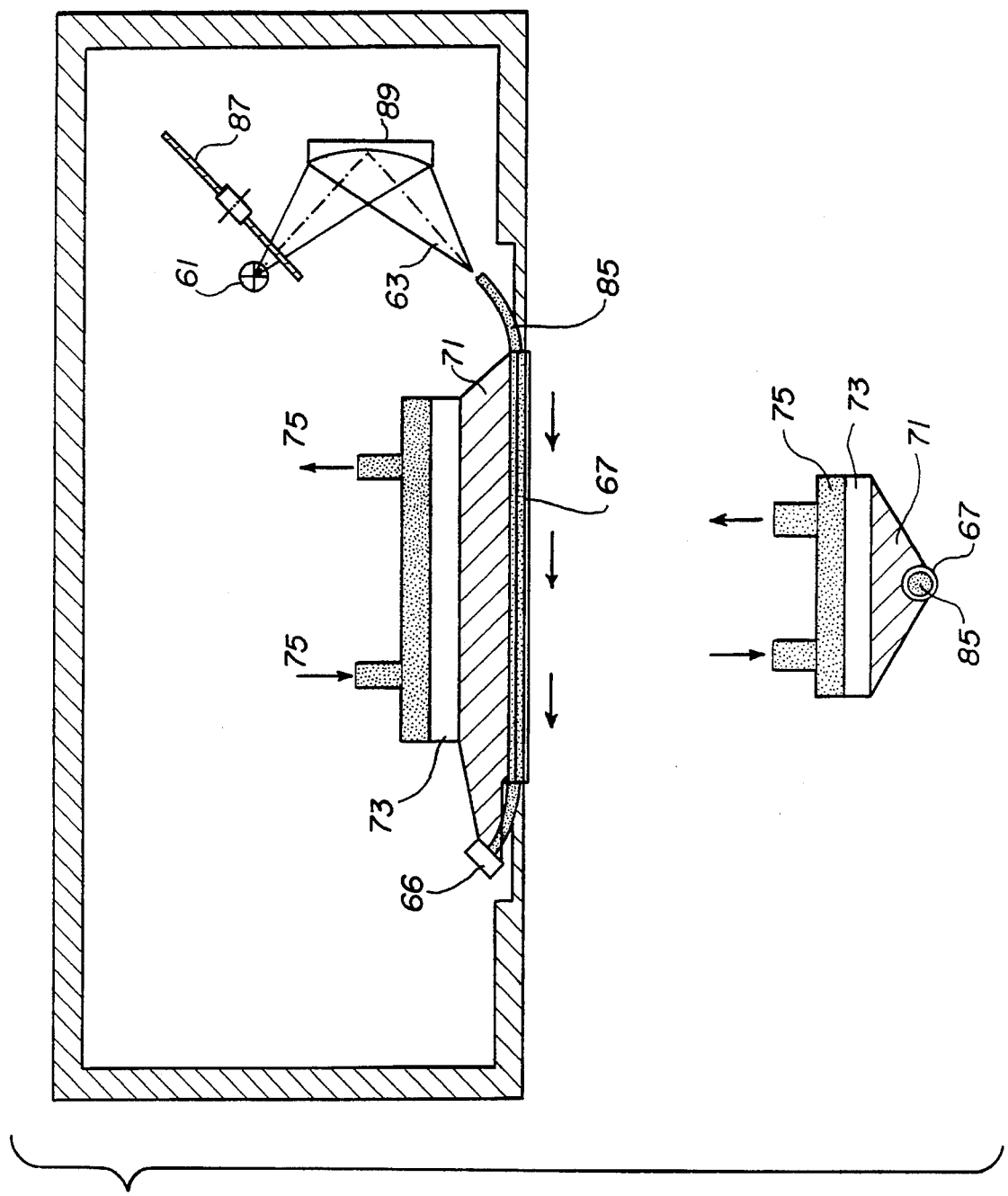
FIG. 3 and FIG. 4 are sectional views of an alternative sensor element of the present invention.

The present invention employs universal laws of thermodynamic equilibria which state that the same concentration of an analyte, extracted by a membrane from water, is reached if there is another gaseous medium added between both media, in which the substance is also in equilibrium with the water as well as with the membrane, provided all the media are at the same temperature, if a thermodynamic equilibrium is reached between two media (for example, water/plastic membrane) and one adds a third medium in between (water/gas/plastic membrane) the same ratio of concentrations in the plastic relative to that in water (Cp/Cw) is reached. Therefore, it does not make a difference regarding the final result if a contaminant (analyte) is extracted by directly placing a plastic analyte extracting membrane in contact with contaminated water or if a contaminant is extracted by allowing an equilibrium to be reached between the contaminated water and a gas and, further, between that gas and the plastic analyte extracting membrane, provided all media have the same temperature. Such media exclude the mechanical impurities which might be present in a contaminated medium sample to be investigated which cannot be fully removed by filtering from destroying an extracting membrane on an ATR crystal or used as cladding on an optical fiber.

Further, by selection of appropriate temperatures at the interfaces, the extraction process can be enhanced considerably. If, for example, the temperature of the contaminated medium to be analyzed is raised and the temperature of the plastic extracting membrane is reduced, there will be an additional distillation process making Cp/Cw much larger by about two orders of magnitude. This effect is maximized in a preferred embodiment of the present invention wherein the contaminated medium to be analyzed for the presence of volatile components is heated to a temperature approaching its boiling point, thereby considerably enhancing the vapor pressure of the volatile components. Further, the sensor element with its surrounding analyte extracting membrane is cooled to just above its freezing point, which serves to further enhance the concentration of the analyte (volatile component to be measured) in the extracting membrane and decrease the limit of detection significantly over prior art methods. A further feature of the new arrangement is that the medium evaporates as well as the analyte and condenses at the surface of the cooled sensor. The condensing distilled medium cleans the surface of the extracting membrane surrounding the sensor. Since the membrane is hydrophobic, the condensing water does not interfere with the measurement of the concentration of the analyte.

The materials employed in the extraction membrane and internal reflection element of the present invention are as disclosed by the prior art. In a preferred embodiment of the present invention, the extracting membrane material is, for example, low density polyethylene, polydimethylsiloxane or a fluorcarbon polymer, a special copolymer or related polymeric material which may be modified to a three (3) dimensional molecular network in order to enhance the stability. The design of the membrane is improved by using modified monomers in order to enhance the enrichment factor as well as to reduce the chemical wear by using the three (3) dimensional polymer network which is absolutely insoluble. Alternatively, the polymer material may be fully deuterated in order to allow determination also of hydrocarbons since there are then no coincidences of absorption bands of the membrane material and the analyte. Hydrogen-substituted membranes result in overlapping characteristic absorptions. The polymer material may cover the surface of any kind of material which may be used as an internal reflecting element in any spectral range. The internal reflecting element must have a larger refractive index than the extracting membrane and it should be transparent in a spectral range where a suitable absorption band of the analyte occurs. A spectral band of the measuring radiation is isolated for the measurement of this band following standard techniques of spectroscopy. The preferable measurement device is interference filters however, other devices such as prisms, gratings and interferometers as well as selective (laser) emitting diodes or wavelength selective detectors may be used. Any drift in sensitivity may be compensated for by using a reference beam in parallel arrangement with a second device. In that instance an analyte can be measured at a wavelength where the analyte absorbs relative to that wavelength. Where the analyte does not absorb, the two devices can be used to measure with the same radiation and detector, with one active polymer membrane and the other isolated from the analyte. Two or even more components may be measured simultaneously by adjusting the wavelength band to the absorption bands of different analytes and/or by employing tunable interference filters. Several (e.g. five) measuring channels can be created using optical fibers as internal reflection elements. In that instance, each channel can be used to measure and record one component separately. The preferred embodiment utilizes a set of light emitting diodes as a light source which emit radiation selectively at the absorption bands of the different components to be analyzed. Alternatively, one common IR source can be used with different optical filters at the entrance of the fibers or an IR prism or grating polychromator with the fiber entrances at proper positions of the spectrum.

The resistance of the membrane against wear may be increased by an improved design of the interface between the internal reflection element and the membrane by using chemical bonding with special primers.

In such a preferred embodiment, the IRE is cooled by a Peltier device which is in contact with the extracting membrane covering the IRE opposite the side of the IRE which faces the distilled sample to be measured. A Peltier element is a thermoelectric cooling system used for cooling photodetectors (to reduce the noise), laser diodes, etc. Physically, it is a reversed thermocouple. The effect was first described by the French physicist Peltier.

Figure 4:
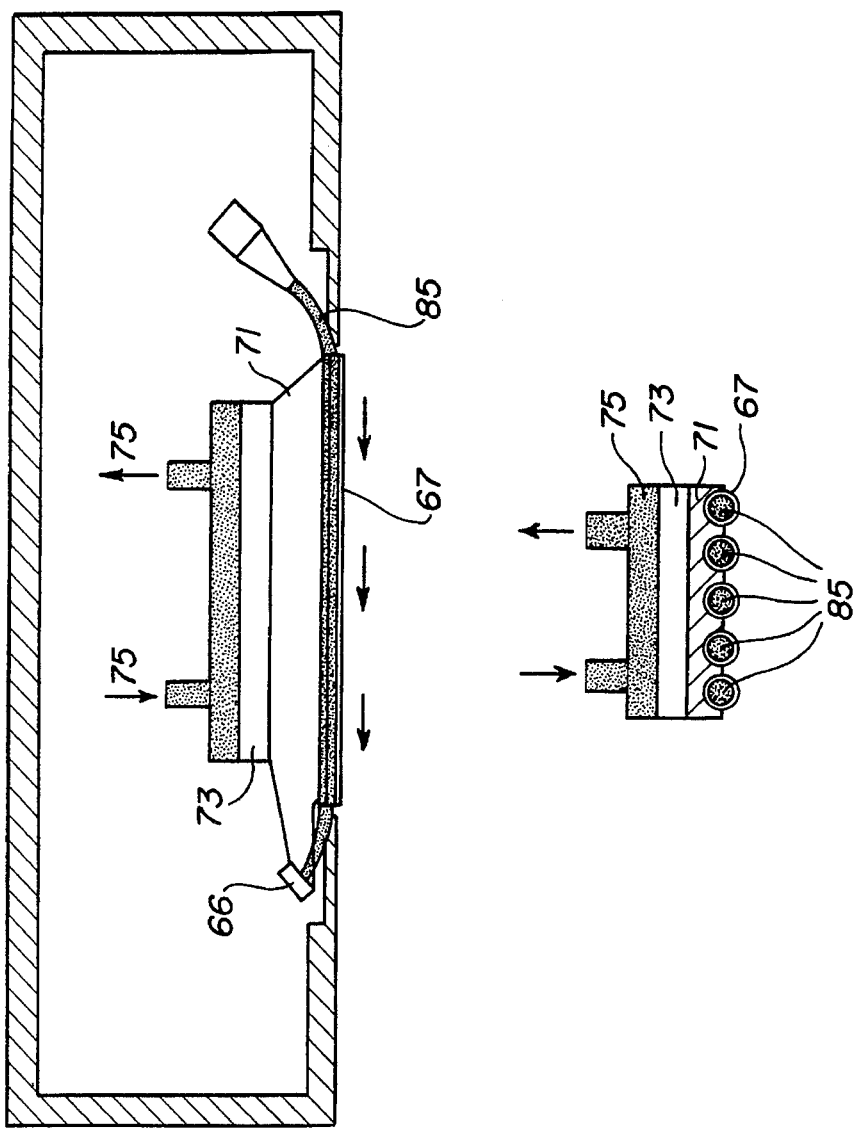

FIG. I shows present invention device 10 with pipe 11 through which a main stream of contaminated medium to be analyzed is running in flow direction indicated by arrow 13. Pump 17 delivers a constant flow of contaminated medium through delivery tube 15 in the direction of flow arrow 21. Continuous flow medium heater 19 brings the medium to a temperature just below its boiling point e.g., 90 degrees centigrade. Sample medium then enters nozzle shaft 23 and exits in a fine mist spray typified by spray line 27 at nozzle head 25.

Special provisions for producing a mist with droplets of a very small radius (e.g. a rotating disk) enhance the vapor pressure. Metal sheets 31, 33 and 35 protruding from the sides of evaporation chamber 29 protect sensor element 37 from the medium spray exiting nozzle head 25 so that extracting membrane 38 employed surrounding sensor element 37 does not come in direct contact with undistilled medium to be investigated. The sample evaporates in evaporation chamber 29 when it comes into contact with sensor element 37 as vapor 36.

Sensor element 37, e.g. an ATR crystal or an optical fiber or a series of them surrounded by an extracting membrane 38 which has been cooled to a temperature just above freezing, e.g. 4 degrees centigrade by cooling means 51. The vapor 36, upon coming in contact with cooled sensor element 37, condenses. Hydrophobic extracting membrane 38 surrounding sensor element 37 selectively absorbs a predetermined analyte or analytes to be optically measured and excludes water. Optical measurement is achieved via radiation source 53 directing an optical radiation beam through sensor element 37 and detecting the amount of analyte being measured by means of a detector unit 55 measuring the attenuation of the so-called evanescent wave. The condensing medium typified by droplets 39, 41, 43 and 45 washes the surface of extracting membrane 38 of sensor element 37. Return tube 47 is provided to return condensed vapor and sprayed sample from evaporation chamber to the main stream. One way valve 49 prevents backwash.

FIG. 2 shows a more detailed cross section view of sensor element 37 relative to cooling device (in this case, a Peltier element) and heated sample vapor 68 to be analyzed in a preferred embodiment of the present invention. Internal reflection element (in this case, a parallelepiped) 65 is surrounded by hydrophobic extracting membrane 67. Hydrophobic extracting membrane 67 which serves further to exclude water and is affixed with an adhesive layer to permit stronger chemical bonding of extracting membrane 67 to internal refection element 65. The extracting membrane 67 is in contact with sample vapor 68 at lower interface 81 and in contact with cooling device 73 (in this case a Peltier element) at upper interface 83 via a copper plate 71. Peltier element 73 utilizes water or air or some other suitable coolant 75 and cools membrane 67 on a site opposite where the membrane 38 is in contact with the sample vapor. Internal reflection element 65 is also in operative connection with a radiation beam source 61 and radiation detector 66. Radiation beam source 61 directs radiation beam 63 through Internal Reflection Element 65 and the measurement of the predetermined volatile analyte is achieved by detector unit 66. The wheel 87 contains optical filters for measuring radiation at the wavelength of the absorption bands of the analyte and at a reference wavelength or for measuring the absorption bands of several analytes plus at a reference wavelength.

FIG. 3 and FIG. 4 show a sectional view of an alternative sensor element 37. Specifically showing the placement of an optical fiber or a series of optical fibers in a parallel arrangement and their contact with the extracting membrane, the sample vapor 68 and the cooling device 73. An optical fiber as IRE is connected to a radiation beam source 61 and radiation detector 66 which measures the analyte. Alternatively a series of fibers may be arranged in parallel each designed for measuring a specific component by using selective sources, optical fibers or selective detectors. FIG. 4 shows five measuring channels using optical fibers as internal reflection elements. This allows for recording of five different components simultaneously. As a light source, a set of light emitting diodes may be used which emit radiation selectively at the absorption bands of the different components to be analyzed. Alternatively, one common IR source can be used with different optical filters (e.g. interference filters) at the entrance of the fibers or an IR prism or grating polychromator with the fiber entrances at proper positions of the spectrum. A set of detectors could be used as an alternative which would only record the radiation within a distinct wavelength range.

Having described the preferred embodiment of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. A method for the optical measurement of the concentration of at least one analyte in a contaminated medium comprising a continuous distillation process of said at least one predetermined analyte into a gaseous medium in close contact with said contaminated medium combined with enhancement of said concentration of said at least one analyte by continuous extraction into a hydrophobic membrane in contact with said gaseous medium, said hydrophobic membrane selectively permeable for said at least one analyte, said hydrophobic membrane defining a measuring space, said measuring space being transparent for a measuring radiation, said measuring space being repellant to the contaminated medium and free from any indicator, said measuring space located on a surface of a light conducting Internal Reflection Element selected from the group consisting of a parallelepiped or a fiber which has a refractive index greater than that of the measuring space, said Internal Reflection Element being impermeable to said at least one analyte to be measured, providing radiation that passes through said internal reflection element being totally reflected at its surface and emerging therefrom as an evanescent wave which is within said measuring space and which is attenuated at wavelengths corresponding to absorption bands of said at least one analyte measuring said wavelength attenuation and correlating the attenuation to that of said analyte.

2. The method of claim 1 wherein said contaminated medium is water.

3. The method of claim 1 wherein said IRE is chosen from the group consisting of ATR crystals and optical fibers.

4. The method of claim 1 wherein said continuous distillation process is enhanced by heating of said contaminated medium up to a temperature near the boiling point of said medium.

5. The method of claim 1 wherein said distillation process is enhanced further by pumping said contaminated medium through a nozzle which generates a fine mist consisting of very small droplets.

6. The method of claim 3 wherein the extracting membrane on the surface of an ATR crystal or an optical fiber is cooled to a temperature just above the freezing point of said medium.

7. The method of claim 4 wherein said extracting membrane is cooled by a Peltier element.

8. The method of the preceding claims wherein several fibers are arranged in parallel permitting the analysis of more than one analyte.

\* \* \* \* \*